US00PP36021P2

(12) United States Plant Patent
Bull

(10) Patent No.: US PP36,021 P2
(45) Date of Patent: Jul. 16, 2024

(54) ***RUDBECKIA* PLANT NAMED 'BULLRUDIHIR 120'**

(50) Latin Name: ***Rudbeckia hirta* L.**
Varietal Denomination: BullRudihir 120

(71) Applicant: Hartwig Bull, Gönnebek (DE)

(72) Inventor: Hartwig Bull, Gönnebek (DE)

(73) Assignee: Hartwig Bull, Gönnebek (DE)

( * ) Notice: Subject to any disclaimer, the term of this patent is extended or adjusted under 35 U.S.C. 154(b) by 0 days.

(21) Appl. No.: 18/413,913

(22) Filed: Jan. 16, 2024

(51) Int. Cl.
*A01H 5/02* (2018.01)
*A01H 6/14* (2018.01)

(52) U.S. Cl.
USPC ..... Plt./474
CPC ..... *A01H 6/14* (2018.05)

(58) Field of Classification Search
USPC ..... Plt./474
CPC ..... A01H 5/02
See application file for complete search history.

*Primary Examiner* — Kent L Bell
(74) *Attorney, Agent, or Firm* — The Webb Law Firm

(57) ABSTRACT

A new and distinct variety of *Rudbeckia* plant having an upright, very compact growth habit and yellow, semi-double inflorescences.

1 Drawing Sheet

Botanical classification: *Rudbeckia hirta* L.
Varietal denomination: 'BullRudihir 120'.

BACKGROUND OF THE INVENTION

The present invention comprises a new and distinct cultivar of *Rudbeckia* plant known by the varietal name 'BullRudihir 120'. The new variety was discovered in August of 2021 in Gönnebek, Germany as the result of a planned breeding program with the purposes of providing *Rudbeckia* plants with improved growth, more uniformity, a compact growth habit, increased branching, attractive foliage, faster crop time, and earlier flowering. The new variety is the result of a cross between an unpatented *Rudbeckia hirta* L. variety having an internal breeder's reference of "BR 19-2020" (female parent) and an unpatented *Rudbeckia hirta* L. variety having an internal breeder's reference of "BR 06-2020" (male parent) from the breeder's own collection. The new variety was first asexually reproduced via in-vitro tissue culture cuttings in Gönnebek, Germany in September of 2021. The new variety is similar to its parental varieties in botanical classification, but exhibits increased branching, more compact growth, and more attractive foliage than both of its parental varieties. Further, 'BullRudihir 120' exhibits semi-double, yellow inflorescences with a faster crop time that distinguish it from its female parent and smaller, semi-double inflorescences with earlier flowering that distinguishes the new variety from its male parent.

When 'BullRudihir 120' is compared to *Rudbeckia hirta* L. variety named 'Amarillo Gold' (unpatented), 'BullRudihir 120' is similar to 'Amarillo Gold' in botanical classification, but 'BullRudihir 120' exhibits semi-double inflorescences, as well as more uniform growth with increased self-branching, and more attractive foliage than 'Amarillo Gold'. Further, the following characteristics distinguish 'BullRudihir 120' when generally compared to other *Rudbeckia* varieties known to the breeder:

Medium sized, semi-double inflorescences;
Good self-branching;

An upright, very compact, and uniform growth habit that makes the new variety suitable for small pot sizes;
Healthy, green foliage;
Long bloom time; and
Fast crop time with very early flowering.

The new variety has been trial and field tested and has been found to retain its distinctive characteristics and remain true to type through successive asexual propagations. The present invention has not been evaluated under all possible environmental conditions. The phenotype may vary with variations in environment without a change in the genotype of the plant.

DESCRIPTION OF THE DRAWING

The accompanying photographic drawing illustrates the new variety at 15 weeks of age, with the color being as nearly true as is possible with color illustrations of this type.

DESCRIPTION OF THE PLANT

The following detailed description sets forth the characteristics of the new variety as the result of asexual reproductions performed via in vitro tissue culture cuttings carried out in Gönnebek, Germany. Plants of the new variety were grown outdoors in 21 cm (4 liter) pots under normal field production conditions. The color readings and measurements were observed outdoors under natural light on 15 week old plants in Gönnebek, Germany. Color references are primarily to The 2015 R.H.S. Colour Chart of The Royal Horticultural Society of London, Sixth Edition, except where terms of ordinary significance are used.

PLANT

Time to initiate roots: About 7-10 days at approximately 18° C.
Time to develop roots: About 35-38 days at approximately 16-18° C.

Time to produce a finished flowering plant from a rooted cutting: About 7-8 weeks in a 21 cm container.
Rooting habit: Exhibits numerous roots of medium thickness that are freely branching and healthy in appearance.
Plant height: 32.0-40.0 cm.
Plant width: 35.0-40.0 cm.
Vigor: High, with an upright, very compact, and uniform growth habit.
Disease/pest resistance: Nothing unusual noted to date.
Temperature tolerance: From −3 to +40° C.
Drought tolerance: Average.
Branching habit: Exhibits one dominant strong branch with several lateral side branches. The lateral branches are upright, forming an attractive habit.
Branches (flowering stems):
*Number per plant.*—15-30.
*Length.*—10.0-35.0 cm.
*Diameter.*—5.0-10.0 mm.
*Internode length.*—2.0-10.0 cm.
*Angle.*—Upright and outward.
*Strength.*—Strong.
*Texture.*—Pubescence present.
*Color.*—Close to Yellow-Green Group RHS 144A to 144B.
Foliage:
*Arrangement.*—Single.
*Leaf.*—Length: 5.0-20.0 cm. Width: 1.5-7.0 cm. Shape: Oblanceolate. Apex: Acuminate. Base: Attenuate to acute. Margin: Dentate and undulate. Texture: Upper surface: Rough, with pubescence present. Lower surface: Rough, with pubescence present. Color: Young leaves: Upper surface: Close to Green Group RHS 137B. Lower surface: Close to Green Group RHS 137C. Mature leaves: Upper surface: Close to Green Group RHS 137A to 137C. Lower surface: Close to Green Group RHS 137D. Petiole: None present. Veins: Venation type: Pinnate. Color: Upper surface: Close to Yellow-Green Group RHS 145C. Lower surface: Close to Yellow-Green Group RHS 145A.

INFLORESCENCE

Bud:
*Diameter.*—2.0-4.0 cm.
*Length.*—2.0-5.0 cm.
*Color.*—Close to Yellow-Green Group RHS 151A.
Appearance: Elliptic-shaped ray florets and tubular-shaped disc florets.
Natural flowering season: Flowering occurs from June-October in Gönnebek, Germany, beginning approximately 7-8 weeks after planting.
Average number of inflorescences per plant: 12-35.
Average number of inflorescences per branch: 1-5.
Disc and ray floret arrangement: Disc florets are arranged in the middle of the receptacle of the composite, semi-double, freely flowering plant, with ray florets extending outwardly therefrom.
Fragrance: Sweet.
Inflorescence:
*Diameter.*—8.0-15.0 cm.
*Height (depth).*—2.0-4.0 cm.
*Diameter of disc.*—2.0-3.0 cm.
*Receptacle height.*—Average of 1.0 cm.
*Receptacle diameter.*—4.0-8.0 cm.
Ray florets:
*Number per inflorescence.*—30-55.
*Arrangement.*—Semi-double, in two to four whorls.
*Length.*—3.0-6.5 cm.
*Width.*—1.5-3.0 cm.
*Shape.*—Elliptical.
*Apex.*—Emarginate.
*Base.*—Acute.
*Margin.*—Entire.
*Texture.*—Upper surface: Smooth and glabrous. Lower surface: Rough.
*Color.*—When opening: Upper surface: Close to Yellow-Orange Group RHS 17A. Lower surface: Close to Yellow-Orange Group RHS 15C. At maturity: Upper surface: Close to Yellow-Orange Group RHS 17C. Lower surface: Close to Yellow-Orange Group RHS 15C. Ground color description: Close to Yellow-Orange Group RHS 17C.
*Venation.*—Appearance: Parallel. Color: Upper surface: Same color as the florets. Lower surface: Same color as the florets.
Disc florets:
*Number per inflorescence.*—Numerous; too many to quantify.
*Arrangement.*—In the center of receptacle.
*Length.*—5.0-10.0 mm.
*Width.*—*About* 1.0 mm.
*Shape.*—Tubular.
*Apex.*—Five-pointed.
*Color.*—Immature: Close to Yellow-Green Group RHS 145A. At maturity: Close to Yellow-Orange Group RHS 20A.
Phyllaries:
*Number per inflorescence.*—25-30.
*Arrangement.*—In three whorls.
*Length.*—1.0-4.0 cm.
*Width.*—3.0-10.0 mm.
*Shape.*—Lanceolate.
*Apex.*—Elongated oval.
*Base.*—Fused.
*Margin.*—Undulate.
*Texture.*—Upper surface: Rough, with pubescence present. Lower surface: Rough, with pubescence present.
*Color.*—Immature: Upper surface: Close to Green Group RHS 138A. Lower surface: Close to Green Group RHS 138B. At maturity: Upper surface: Close to Green Group RHS 138A. Lower surface: Close to Green Group RHS 138B.
Reproductive organs:
*Androecium.*—Presence: On disc and ray florets. Number (per floret): Numerous; too many to quantify. Filament length: 1.0-2.0 mm. Filament color: Close to Yellow-Orange Group RHS 20A. Anther: Shape: Oval. Length: 1.0 mm. Color: Close to Yellow-Orange Group RHS 20A. Pollen: Color: Close to Yellow-Orange Group RHS 17A. Amount: Plentiful — too much to quantify.
*Gynoecium.*—Presence: On disc florets. Pistil length: About 2.0 mm. Stigma: Shape: Two-parted. Color: Close to Yellow-Orange Group RHS 20A. Style: Length: 1.0-2.0 mm. Color: Close to Yellow-Orange Group RHS 20A.
Seeds:
*Overall size.*—Approximately 2.0 mm.
*Color.*—Close to Black Group RHS 202A.

I claim:

1. A new and distinct variety of *Rudbeckia* plant named 'BullRudihir 120', as is herein illustrated and described.

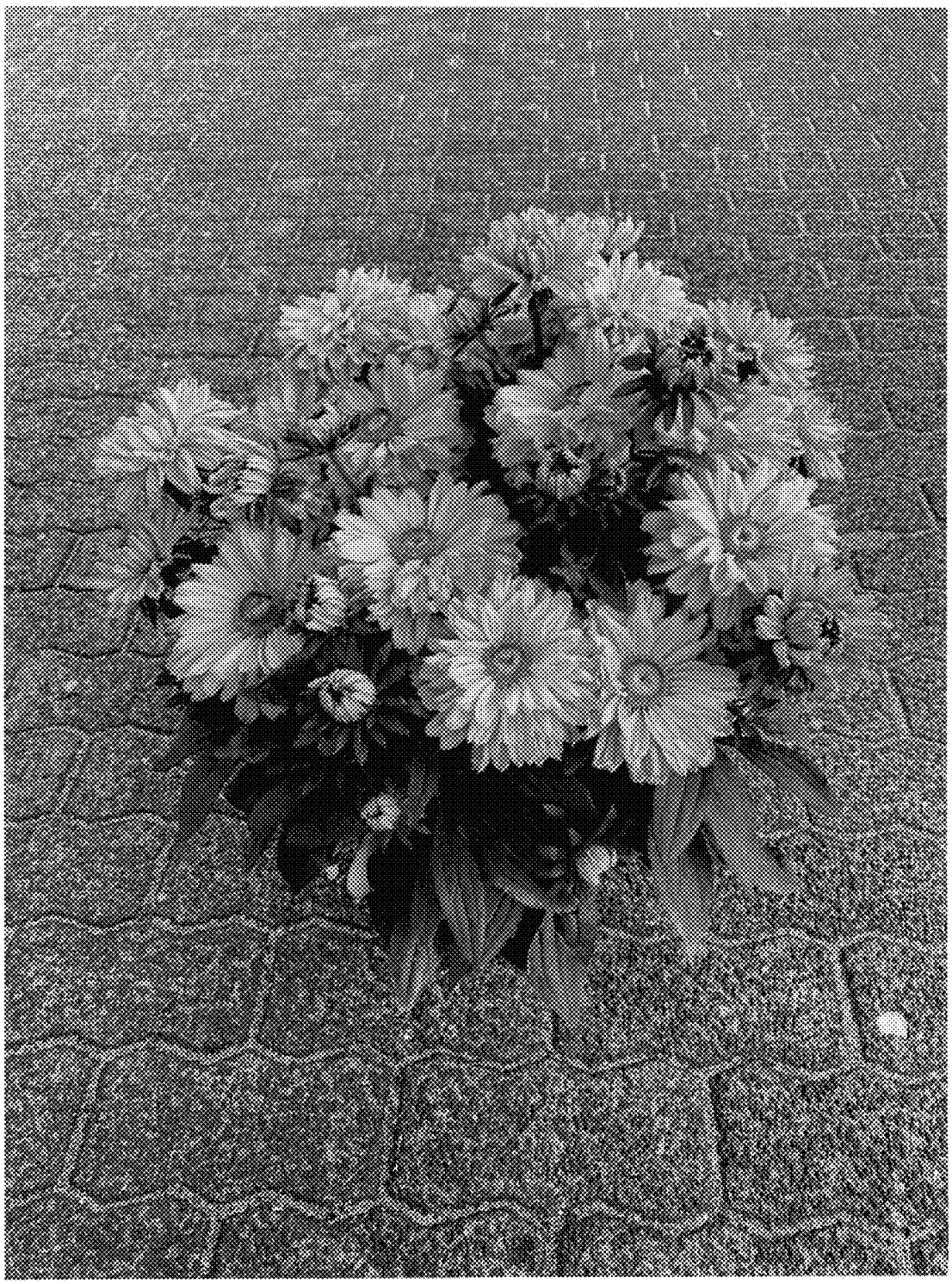

* * * * *